United States Patent
Kfoury et al.

(10) Patent No.: US 7,191,071 B2
(45) Date of Patent: Mar. 13, 2007

(54) METHOD OF DETERMINING THE COMPONENTS OF AN EFFECTIVE PERMEABILITY TENSOR OF A POROUS ROCK

(75) Inventors: Moussa Kfoury, Saint-Priest (FR); Benoit Noetinger, Rueil Malmaison (FR); Michel Quintard, Montastruc-la-Conseillere (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 11/001,035

(22) Filed: Dec. 2, 2004
(Under 37 CFR 1.47)

(65) Prior Publication Data
US 2005/0229680 A1 Oct. 20, 2005

(30) Foreign Application Priority Data
Dec. 2, 2003 (FR) .................................. 03 14211

(51) Int. Cl.
*G06F 19/00* (2006.01)
(52) U.S. Cl. ....................................................... 702/32
(58) Field of Classification Search .................... 702/32
See application file for complete search history.

(56) References Cited

OTHER PUBLICATIONS

Durlofsky, Louis J., "Numerical Calculation of Equivalent Grid Block Permeability Tensors for Heterogeneous Porous Media," Water Resources Research, vol. 27, No. 5, pp. 699-708, May 1991, USA.
Bernabé, Yves, "Chapter 6: On the Measurement of Permeability in Anisotropic Rocks," Fault Mechanics and Transport Properties of Rocks, copyright 1992, Academic Press Ltd. pp. 147-167.
Renard, Phillippe, et al, "Laboratory Determination of the Full Permeability Tensor," J. of Geophysical Research, vol. 106, No. 811, pp. 26,443-26,452.

*Primary Examiner*—John Barlow
*Assistant Examiner*—Jonathan Moffat
(74) *Attorney, Agent, or Firm*—Antonelli, Terry, Stout and Kraus, LLP.

(57) ABSTRACT

The invention is a method of determining all the components of an absolute permeability tensor of a porous medium sample from permeability measurements, obtained for example by placing the sample in a permeameter which is useful for fast determination of permeability anisotropies of rocks and detention of internal heterogeneities. A pressure difference ΔP is applied between the inlet and outlet faces of a laboratory rock sample, with zero flow conditions on the edges parallel to the mean flow obtained by confining it in a sheath under pressure. Starting from conventional permeability measurements in three directions and from the measurements of the two components of the viscous forces transverse to the sample, a permeability tensor k can be "inverted" by numerical solution of the corresponding boundary-value problem. Since these quantities can be alternatively obtained from numerical solutions of the same flow in a heterogeneous medium, the method can also be used as an upscaling tool in a reservoir simulator.

8 Claims, 4 Drawing Sheets

METHOD OF DETERMINING THE COMPONENTS OF AN EFFECTIVE PERMEABILITY TENSOR OF A POROUS ROCK

BACKGROUND OF THE INVENTION

1. Field of the Invention

The present invention relates to a method of determining all of the 2D or 3D components of an absolute permeability tensor of a porous medium sample and/or allowing scaling of heterogeneous permeability fields, from data measured in the laboratory or from underground zone permeability maps provided by geologists.

2. Description of the Prior Art

Laboratory measurement of the permeability of rocks are a key stage in oil reservoir, aquifer, civil engineering surveys, or even the study of catalysts used in the chemical industry. If a medium exhibits obvious anisotropy directions, the experimenter will try to respect them during measurement survey. In other words, the experimenter will position along proper axes of the permeability tensor. There are cases where this direction is not given beforehand and the tensor therefore has to be determined a priori without preconceived ideas. It can also turn out that the rock samples have not been cored in the right directions; furthermore, the proper axes of the tensor are not necessarily aligned with the bedding exhibited by some rock samples.

It is therefore particular useful to have direct measurements of all the components of the tensor, or at least to estimate the possible anisotropy thereof.

A method of determining a permeability tensor of a rock sample from measurements allowing estimation of, with sufficient accuracy, the mean pressures around a sample placed in a permeameter suited to the measurements thereof is described for example in the following publication:

Renard P. "*Laboratory Determination of the Full Permeability Tensor*" JGR 106, B11 2001 pp 26 443–26 451.

Another known method of determining a permeability tensor wherein flows which are made deliberately tortuous by changes in the boundary conditions of the injection faces are created in the sample and wherein an inverse problem is solved is for example described in the following publication:

Bernabé Y.: "*On the Measurement of Permeability in Anisotropic Rocks*" in "Fault Mechanics and Transport Properties of Rocks" edited by B. Evans and T F Wong pp 147–167, Academic San Diego 1992.

In order to be implemented, the known methods require substantial changes in the flow conditions, which makes them costly and difficult to be applied in practice.

Within the context of upscaling, well-known to reservoir engineers, laboratory experiments are replaced by the results of a "fine" numerical simulation on the heterogeneous medium, in order to replace it by an equivalent homogeneous medium whose permeability tensor is for example denoted by $K_{\mathit{eff}}$. In the case of an anisotropic medium, the fine reference simulation is generally performed by considering periodic boundary conditions. Most authors wrongly consider that these are the only conditions allowing obtaining all the elements of the tensor $K_{\mathit{eff}}$.

As shown in the description hereafter, a suitable interpretation of a numerical simulation of the same permeameter can provide this information. The boundary conditions applied in a permeameter can be more realistic in the case where the large-scale flow is constrained by clay barriers. Furthermore, the comparison between the two resulting tensors can provide information on the scale of the Representative Elementary Volume (REV).

SUMMARY OF THE INVENTION

A method according to the invention allows determination, from known permeability measurements, all the components of an absolute permeability tensor ($K_{eq}$) of a sample of an anisotropic porous medium. The method of the invention essentially comprises the following steps:

measuring or calculating, by applying two liquid flows successively in two (or three) orthogonal directions (Ox, Oy) (and Oz) through the sample and under an imposed pressure gradient, quantities representing the liquid flow rates and the transverse forces generated in the sample by passage of the liquid, the quantities being brought back to unitary pressure gradients; and using a simulator to determine step by step, from an a priori numerical solution of a confined flow in a homogeneous medium, components of the equivalent tensor (k) by means of any inverse method so that corresponding quantities substantially adjust to the measured or calculated quantities.

According to a first implementation mode, the quantities are measured by means of a permeameter and by means for measuring transverse forces applied to the sample in response to flows imposed through the sample.

The transverse forces applied to the sample in response to flows imposed therethrough can be measured for example by measuring weight variations of the sample in the permeameter when the direction of circulation of the liquid flows imposed through the sample is alternated. The other component can be measured by repeating this procedure after a 90° rotation of the sample about an axis parallel to the flow.

According to a second implementation mode, the same quantities can be determined by simulation of flows in a medium, from known or estimated permeability data such as permeability maps provided, for example, by geologists in geophysical applications.

Implementation of the method according to the invention is advantageous in that it allows to simplify and to accelerate determination of the permeability tensor of samples.

BRIEF DESCRIPTION OF THE DRAWINGS

Other features and advantages of the method according to the invention will be clear from reading the description hereafter of a non limitative example, with reference to the accompanying drawings wherein.

DETAILED DESCRIPTION OF THE INVENTION

Figure 5:
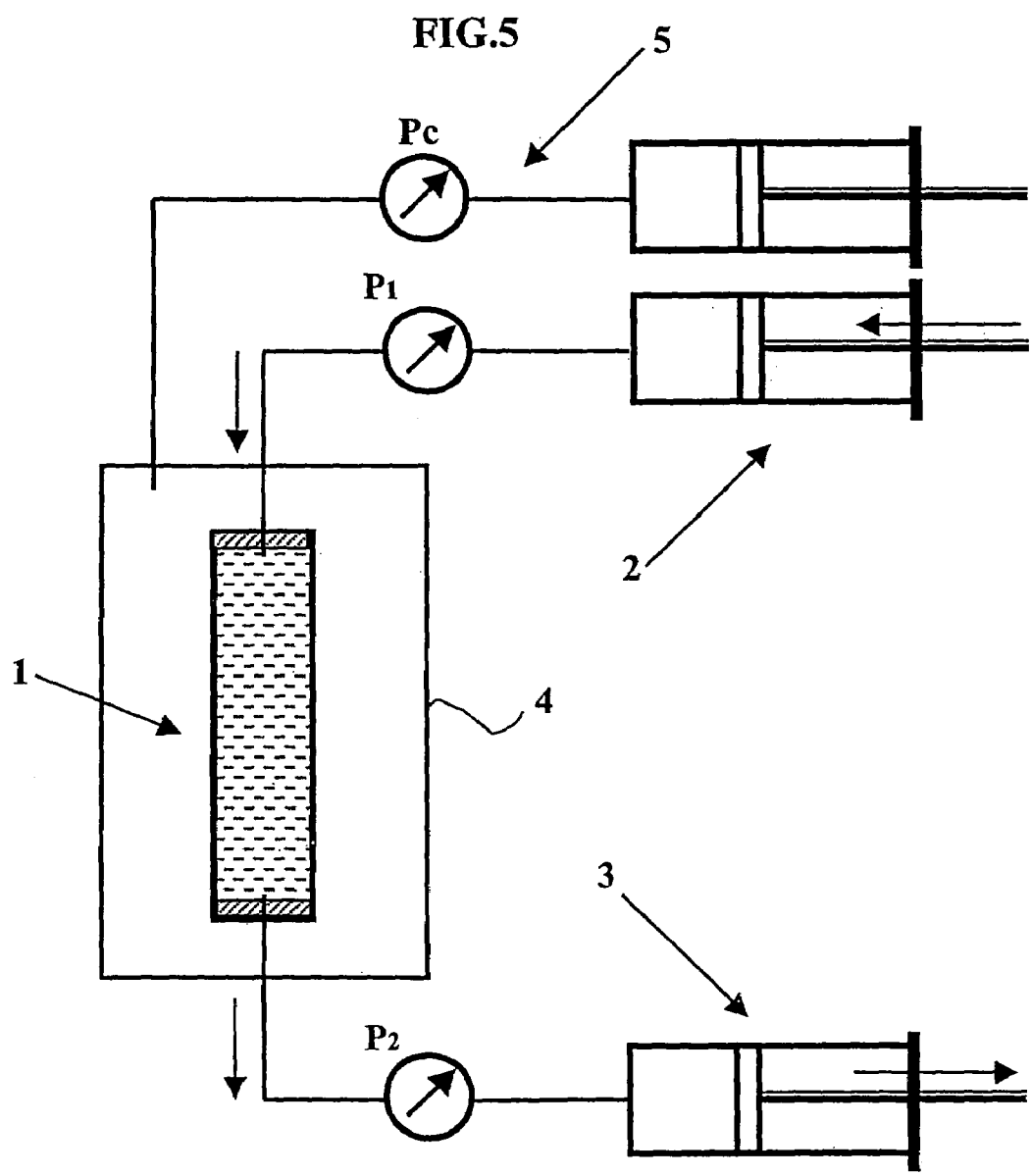
FIG. 5 shows a diagrammatic example of a prior art permeameter suited for measurements on a rock sample.

The permeability measurements useful for implementation of the method described hereafter can be obtained by means of a permeameter of a well-known type. Such a permeameter comprises for example (FIG. 5) a containment cell 1 for the sample. The lateral wall of the cell is a deformable sheath. At a first end, cell 1 is connected to a circuit 2 for injecting a fluid at an injection pressure P1. At the opposite end thereof, the cell is connected to a circuit 3 for discharge of the fluid coming from the sample maintained at a pressure P2. Cell 1 is placed in an outer enclosure 4 connected to a device 5 for applying a confining pressure Pc to the sample, so that the flow of liquid on laterally surrounding the sample is zero (impermeable edges). The opposite terminal parts of cell 1 are such that pressures P1 and P2 respectively exerted on the upstream and downstream faces of the sample are uniform. The quantity $\Delta P_{x,x}$ equals the quantity $P_2-P_1$.

In order to simplify the presentation, a 2D porous medium is considered which is, square, of side L. The method transposed to 3D cases with any proportions is described hereafter. In this part, the porous rock sample is considered to be homogeneous but with a permeability tensor k whose proper axes do not necessarily coincide with the axes of the permeameter where it is placed (FIG. 1).

Figure 1:
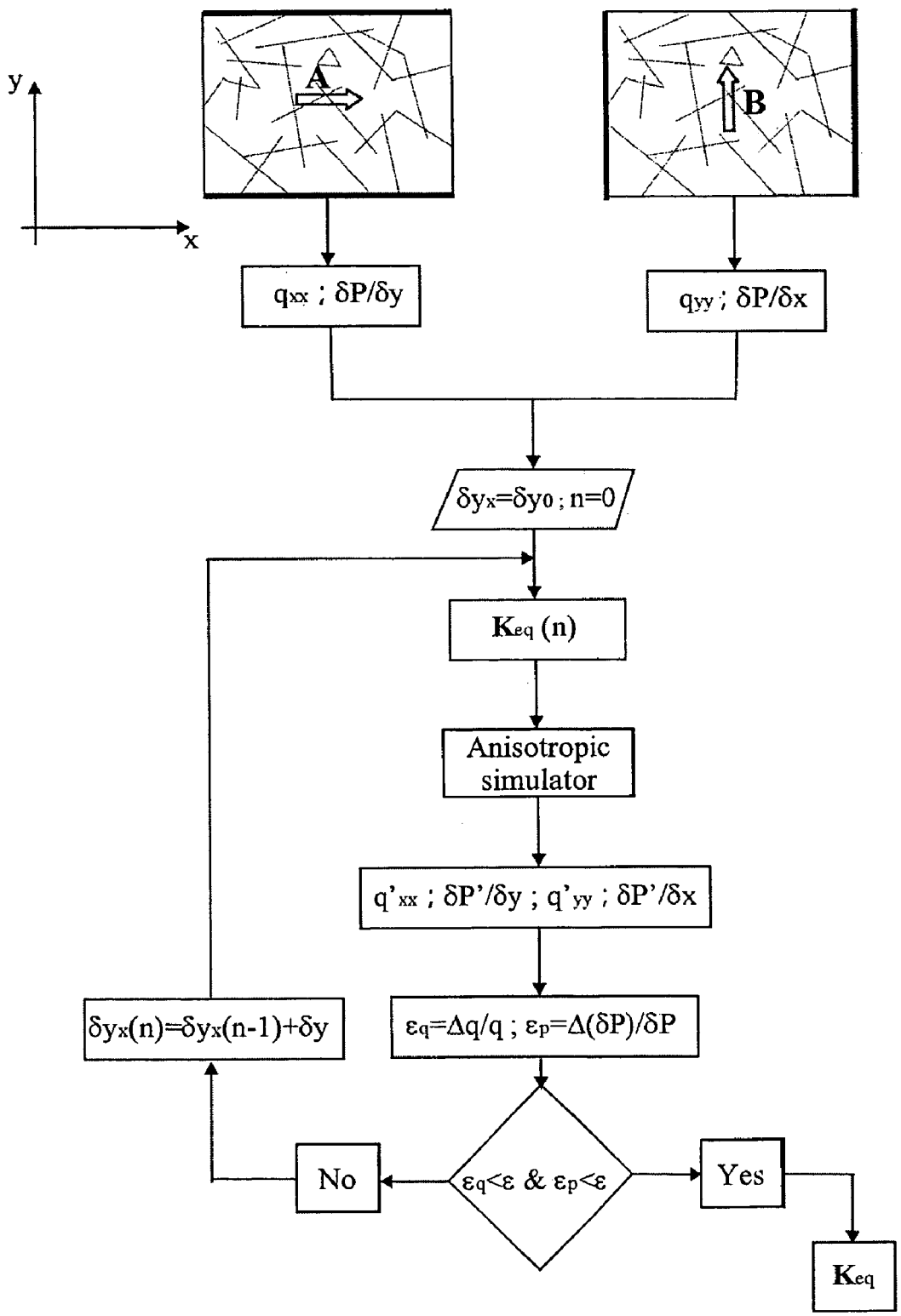
FIG. 1 shows a flowchart allowing iterative determination of the equivalent tensor $K_{eq}(n)$ of a rock sample, from various flow rate and force measurements performed by confining it in a permeameter.

With reference to FIG. 1, the liquid flow is first applied to the sample oriented in a first direction A in relation to the axis of the cell and a series of measurements described below is performed. The experiment is then repeated after orienting the sample in a direction B orthogonal to the first direction, and the same measurements are performed according to the same protocol.

On the faces of the sample parallel to the imposed flow, the standard Neumann zero flow conditions are present, that is:

$$n.k.\nabla p(r)=0 \qquad (1)$$

where r is the spatial position vector of components x, y (or $x_1$, $x_2$), n is the unitary vector orthogonal to the boundary at the point considered, and $\nabla p(r)$ is the pressure gradient. Component by component, a formula is written as follows:

$$\sum_{i,j=1,D} n_i \cdot k_{ij} \cdot \frac{\partial p(r)}{\partial x_j} = 0,$$

or more concisely, by adopting from now on the Einstein summation convention on the repeated indices:

$$n_i k_{ij} \frac{\partial p(r)}{\partial x_j} = 0 \qquad (2)$$

Pressure equation: the pressure equation is given conventionally, the point (•) corresponding to tensor contractions:

$$\nabla \cdot \left( \frac{k}{\mu} \cdot \nabla p(r) \right) = 0 \qquad (3)$$

i.e., in extenso, still with the Einstein convention:

$$\frac{\partial}{\partial x_i} \left[ k_{ij} \frac{\partial p(r)}{\partial x_j} \right] = 0 \qquad (4)$$

The pressure equation and the boundary conditions define a problem denoted by problem (P), well set and having a single solution. In the particular case where direction x coincides with a proper axis of k, the linear solution $$p(x,y,z) = P_1 + \Delta P_{x,x} \cdot \frac{x}{L}$$

is the single solution to the problem. What is obtained, in this case, is the conventional relation $$Q_{x,x} = -k_{x,x} \frac{\Delta P_{x,x}}{\mu}$$

from which $k_{x,x}$ is inferred if $Q_{x,x}$ and $\Delta P_{x,x}$ have been measured simultaneously.

In the general anisotropic case, solution p(x, y, z) has no simple structure and there is no known analytical solution. Therefore the assumption of that the situation presented above is applicable and in practice estimations of the proper values of tensor k are provided.

It is now shown that, provided that some additional quantities are measured, it is possible to determine all the elements $k_{ij}$ of tensor k. Therefore, it is observed that equation (4) can be rewritten in the form as follows:

$$\int_V d^D r \frac{\partial}{\partial x_i} \left[ k_{ij} \frac{\partial p(r)}{\partial x_j} \right] f(r) = 0 \, \forall \, f(r) \qquad (5)$$

where r is the D-component position vector and $d^D r$ the integration element. By selecting then function f(r) suitably (f(r)=x, y then z) in 3D, by integrating by parts the previous equality, the following set of equalities in 2D is obtained:

$$\mu q_{xx} = k_{xx} \frac{1}{L^2} \int_0^L dy (p(x=L,y) - p(x=0,y)) +$$
$$k_{xy} \frac{1}{L^2} \int_0^L dx (p(x,y=L) - p(x,y=0))$$

i.e., with more condensed notations:

$$\mu q_{xx} = k_{xx} \left\{ \frac{\partial p}{\partial x} \right\}_x + k_{xy} \left\{ \frac{\partial p}{\partial y} \right\}_x \qquad (6)$$

$$\mu \delta y_x q_{xx} = k_{yx} \left\{ \frac{\partial p}{\partial x} \right\}_x + k_{yy} \left\{ \frac{\partial p}{\partial y} \right\}_x \qquad (7)$$

where $q_{xx}$ corresponds to the flow rate normalized by the volume of sample $q_{x,x}=Q_{x,x}$ N. The $\{\ldots\}_x$ designate a spatial mean and index x represents here the direction of the pressure gradient imposed. Quantities $\delta y_x$ and $\delta x_y$ are defined by:

$$\delta y_x = \frac{\int_0^L y k_{xx}\left[\frac{\partial p}{\partial x}(L,y) - \frac{\partial p}{\partial x}(0,y)\right]dy}{\int_0^L k_{xx}\frac{\partial p}{\partial x}(0,y)dy}$$

$$= \frac{\int_0^L y k_{xx}\left[\frac{\partial p}{\partial x}(L,y) - \frac{\partial p}{\partial x}(0,y)\right]dy}{V q_{xx}}$$

This quantity corresponds to the difference of coordinates y of the barycenters of the flow rates in local x on the downstream and upstream faces of the sample during a flow imposed in direction x. Similarly, the following relationship is applicable:

$$\delta x_y = \frac{\int_0^L x k_{yy}\left[\frac{\partial p}{\partial y}(x,L) - \frac{\partial p}{\partial y}(x,0)\right]dx}{\int_0^L k_{yy}\frac{\partial p}{\partial y}(x,0)dx}$$

$$= \frac{\int_0^L x k_{yy}\left[\frac{\partial p}{\partial y}(x,L) - \frac{\partial p}{\partial x}(x,0)\right]dx}{V q_{yy}}$$

Similar formulas can be shown by means of the same 3D technique, introducing the three flow rates $q_{xx}$, $q_{yy}$, $q_{zz}$, the six quantities ($\delta y_x$, $\delta z_x$, $\delta x_y$, $\delta z_y$, $\delta x_z$ and $\delta y_z$) and the six additional other quantities $$\left(\left\{\frac{\partial p}{\partial y}\right\}_x, \left\{\frac{\partial p}{\partial z}\right\}_x, \left\{\frac{\partial p}{\partial x}\right\}_y, \left\{\frac{\partial p}{\partial z}\right\}_y, \left\{\frac{\partial p}{\partial y}\right\}_z, \left\{\frac{\partial p}{\partial y}\right\}_z\right).$$

The Dirichlet conditions on the upstream and downstream faces of course provide the relation $$\left\{\frac{\partial p}{\partial x}\right\}_x = \frac{\Delta P_{xx}}{L}.$$

Considering an experiment carried out in another orthogonal direction, the following relationships are obtained:

$$\mu q_{yy} = k_{yx}\left\{\frac{\partial p}{\partial x}\right\}_y + k_{yy}\left\{\frac{\partial p}{\partial y}\right\}_y \tag{8}$$

$$\mu \delta x_y q_{yy} = k_{xx}\left\{\frac{\partial p}{\partial x}\right\}_y + k_{xy}\left\{\frac{\partial p}{\partial y}\right\}_y \tag{9}$$

In order to simplify the notations, unitary imposed pressure gradients $$\left\{\frac{\partial p}{\partial x}\right\}_{x\,ou\,y} = \frac{\Delta P_{xx\,ou\,yy}}{L} = 1$$

are utilized. By inverting these equalities, in this case the following relations are obtained:

$$k_{xx} = \frac{q_{xx} - q_{yy}\delta x_y \left\{\frac{\partial p}{\partial y}\right\}_x}{1 - \left\{\frac{\partial p}{\partial x}\right\}_y \left\{\frac{\partial p}{\partial y}\right\}_x} \tag{10}$$

$$k_{yy} = \frac{q_{yy} - q_{xx}\delta y_x \left\{\frac{\partial p}{\partial x}\right\}_y}{1 - \left\{\frac{\partial p}{\partial y}\right\}_x \left\{\frac{\partial p}{\partial x}\right\}_y} \tag{11}$$

$$k_{xy} = -\left\{\frac{\partial p}{\partial x}\right\}_y k_{xx} + \delta x_y q_{yy} \tag{12}$$

$$k_{yx} = -\left\{\frac{\partial p}{\partial y}\right\}_x k_{yy} + \delta y_x q_{xx} \tag{14}$$

These relations can be grouped together in a symbolic form:

$$k = F\left(q_{xx}, q_{yy}, \left\{\frac{\partial p}{\partial x}\right\}_y, \left\{\frac{\partial p}{\partial y}\right\}_x, \delta y_x, \delta x_y\right). \tag{15}$$

To sum up, in the 2D homogeneous case, by measuring quantities $$q_{xx}, q_{yy}, \left\{\frac{\partial p}{\partial x}\right\}_y, \left\{\frac{\partial p}{\partial y}\right\}_x, \delta y_x, \delta x_y,$$

tensor k can be found directly. Since the tensor is defined by three 2D numbers and six 3D numbers (but, in this case, fifteen additional quantities are determined), this means that there are implicit relations between quantities $$q_{xx}, q_{yy}, \left\{\frac{\partial p}{\partial y}\right\}_x, \left\{\frac{\partial p}{\partial x}\right\}_y, \delta y_x, \delta x_y.$$

In theory, if at least three values are maintained, it should still be possible to find k.

The following subset is maintained:

$$q_{xx}, q_{yy}, \left\{\frac{\partial p}{\partial y}\right\}_x, \left\{\frac{\partial p}{\partial x}\right\}_y \tag{16}$$

The main interest of these data is to have an immediate physical sense so that they can be directly measured: $q_{xx}$, $q_{yy}$ correspond to the usual flow rates (brought back to the volume of the experiment). Quantities $$\left\{\frac{\partial p}{\partial y}\right\}_x, \left\{\frac{\partial p}{\partial x}\right\}_y$$

are measurable because:

$$\left\{\frac{\partial p}{\partial y}\right\}_x = \frac{1}{L^2}\int_0^L dx(p(x, y=L) - p(x, y=0))$$

is merely a resultant of the transverse force per volume unit applied to the sample. Furthermore, by using the general relation:

$$\frac{1}{V}\int_V d^D r \nabla p(r) = \frac{1}{V}\int_{\partial V} d^{D-1} rp(r)n,$$

it is seen that this interpretation of the mean pressure gradient in terms of surface force exerted on the sample remains.

All these quantities or forces can be measured directly in the laboratory. To measure the transverse forces, it is possible to use, for example, dynamometers or strain gages applied locally against the lateral walls of the sample in its sheath (See FIG. 5).

To measure the resultant of the transverse forces more conveniently, it is also possible to measure the weight variations of the sample according to whether the transverse forces are added to or are subtracted from its static weight. All things being equal, a flow is created through the sample successively in a first direction and in the opposite direction. In the first case, the transverse force adds for example to the weight of the cell and, in the other case, it is deducted therefrom. By subtracting the measurements, the measurement of the transverse force can be directly obtained. For implementation, enclosure 4 (see FIG. 5) is placed horizontally on a weighing device (not shown). The weight variation is measured for two positions oriented 90° apart, corresponding to directions A and B shown by arrows in FIG. 1.

2D Example

It is assumed that the quadruplet $$q_{xx}, q_{yy}, \left\{\frac{\partial p}{\partial y}\right\}_x, \left\{\frac{\partial p}{\partial x}\right\}_y$$

of measurements of the flow rates, and transverse forces applied to the sample in the successive positions imposed thereon in the permeameter (four global 2D force and flow rate measurements, nine 3D measurements) is obtained. From now on, the porous media considered can be heterogeneous, that is characterized by a fine map of permeability tensors depending on the position k(r) that can be provided by the geologist or any other technique.

In order to go back to tensor k, $-K_{eq}$ is denoted to identify that it is an effective tensor—from knowledge of $$q_{xx}, q_{yy}, \left\{\frac{\partial p}{\partial y}\right\}_x, \left\{\frac{\partial p}{\partial x}\right\}_y,$$

it is necessary to have a numerical solution to the anisotropic Laplace equation. Any known inversion method can be used. The user can select, for example, an "optimization" method (to minimize the difference between the measured values of $$q_{xx}, q_{yy}, \left\{\frac{\partial p}{\partial y}\right\}_x, \left\{\frac{\partial p}{\partial x}\right\}_y$$

and the predictions of the numerical model), a trial-and-error method, a dichotomy method, etc. An example is given hereafter.

In order to find the tensor $K_{eq}$, associated with the equivalent homogeneous medium, a numerical simulator of a well-known type available on the market is used, operating by finite elements or volumes, to solve the 2D (or 3D) boundary-value problem. The procedure, for example, constructs a sequence of tensors $K_{eq}(1), \ldots, K_{eq}(n)$, etc., defined by its first term representing a first estimation of $K_{eq}$ obtained using relation (15):

$$K_{eq}(1) = F\left(q_{xx}, q_{yy}, \left\{\frac{\partial p}{\partial y}\right\}_x, \left\{\frac{\partial p}{\partial x}\right\}_y, 0, 0\right),$$

Since the moments $\delta y_x$ and $\delta x_y$ are unknown, because they have not been measured, this can only be an approximation since, as discussed above, there is an implicit relation between the moments and $$q_{xx}, q_{yy}, \left\{\frac{\partial p}{\partial y}\right\}_x, \left\{\frac{\partial p}{\partial x}\right\}_y.$$

This first estimation does not take it into account and must therefore be corrected. The estimation of $K_{eq}(n)$ is modified for example by means of the following recurrence relation:

$$K_{eq}(n+1) = F\left(q_{xx}, q_{yy}, \left\{\frac{\partial p}{\partial y}\right\}_x, \left\{\frac{\partial p}{\partial x}\right\}_y, \delta x_y^n, \delta y_x^n\right).$$

Here, quantities $\delta x_y^n$, $\delta y_x^n$ are calculated by means of the numerical simulator: the boundary-value problem (P) is solved by taking as the permeability tensor the previous estimation $K_{eq}(n)$. The iterations are stopped once the quantities $$\left\{q'_{xx}, q'_{yy}, \left\{\frac{\partial p}{\partial y}\right\}'_x, \left\{\frac{\partial p}{\partial x}\right\}'_y\right\}$$

calculated by the simulator with the corresponding estimation $K_{eq}(n)$ are $\epsilon$ from the desired value, $\epsilon$ being a stop criterion set by the user in relation to a norm selected beforehand. The flowchart is given in FIG. 1.

The measurement quadruplet used to completely determine tensor k may also have been calculated by means of a "fine simulation" of the experiment on a heterogeneous medium whose equivalent permeability tensor is to be defined by means of this method. The permeability of this medium is known entirely or partly, for example on the basis of a permeability map provided by the geologist. During this simulation, the Darcy's laws are applied to the flows in the medium and the applicable quadruplet of values is deduced therefrom.

Validation

By simulation, the existence of transverse forces are checked, measurable and quite significant in some cases, which appear when a stream flows through a confined medium, due to the presence of internal heterogeneities or to an anisotropy of the medium, and the possibility of identifying all the components of the equivalent permeability tensor by means of simple measurements of forces on samples obtained by means of a permeameter has been validated. Furthermore, this study allows establishing the error made on the behavior of an equivalent medium (defined by one method or another) in relation to the behavior of the real medium to be homogenized. It is on this basis of a better adjustment between the respective behaviors that the method according to the invention was developed.

Figure 2A:
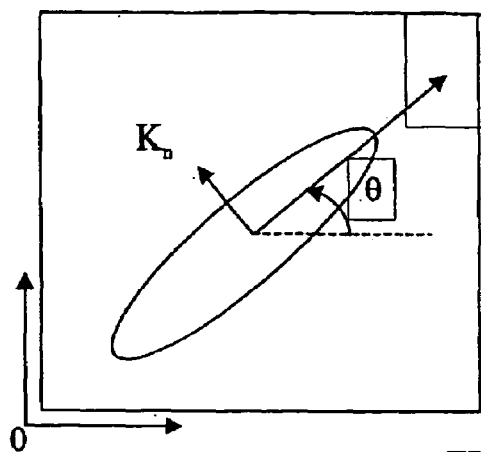
FIGS. 2 to 4 illustrate various simulation examples showing the relevance of the method, which will be discussed in the course of the description.
Figure 2B:
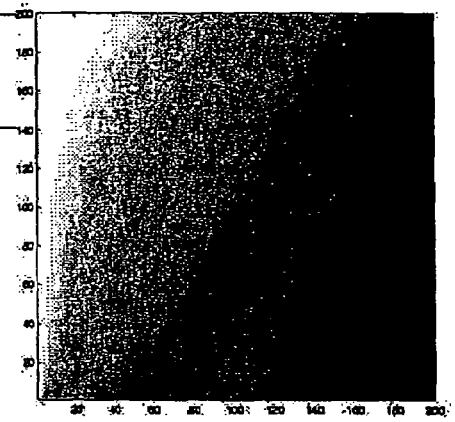
Figure 2C:
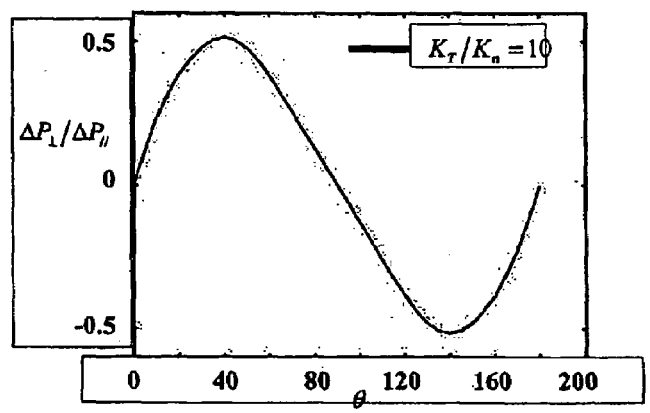

FIG. 2B shows the evolution of the pressure field for an anisotropic homogeneous medium with an anisotropy ratio 10 and where the principal axes of the diagonal tensor (FIG. 2A) are oriented 45° to the horizontal ($\theta$=45°). FIG. 2C shows the evolution of the ratio of the cumulative pressure difference on the impermeable edges (edges perpendicular to the imposed pressure fields) to the pressure difference applied to the inlet-outlet of the medium (edges parallel to the imposed pressures) for $\theta$ (0°$\leq\theta\leq$180°).

Figure 3A:
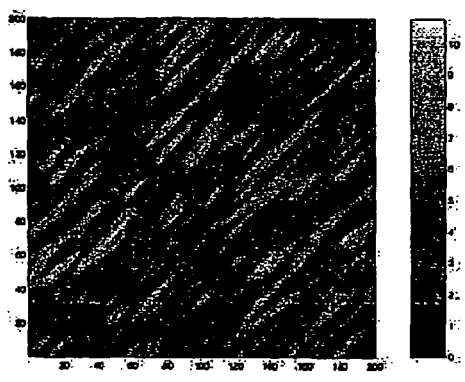
Figure 3B:
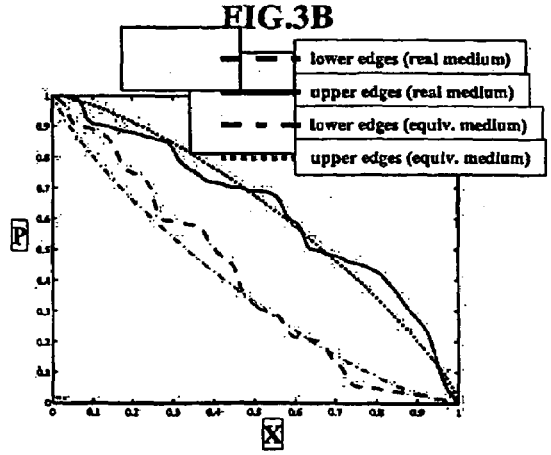
Figure 3C:
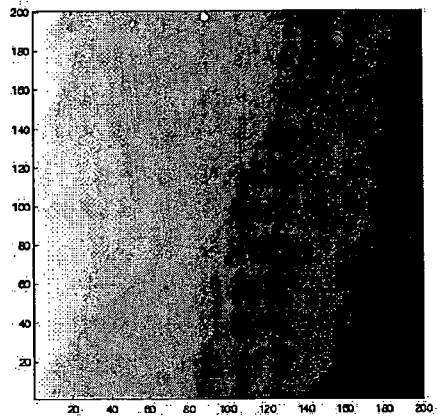
Figure 3D:
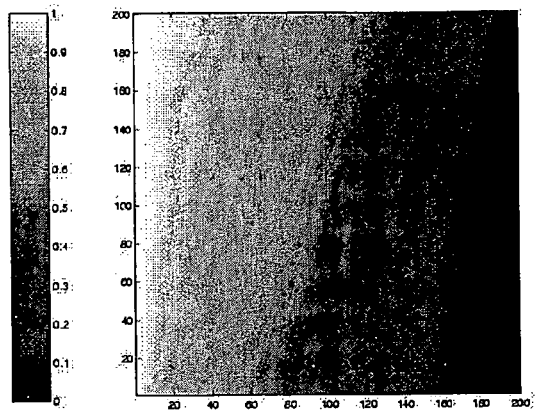

FIG. 3A shows a lognormal permeability map (geometric mean Kg=121, $\sigma^2$=2) generated with the known stochastic generation code FFTAM. Locally, the permeability is isotropic (scalar), on the other hand its correlation function is spatially anisotropic, oriented 45°. FIG. 3B shows the evolution of the pressure on the upper and lower edges (impermeable edges for a horizontal confined flow) for the real medium and its anisotropic homogeneous equivalent determined by means of the permeameter method. FIGS. 3C and 3D respectively show the mappings of the pressure field for the real medium (left) and the equivalent medium (right). After inversion, the components of the permeability tensor of the equivalent medium are estimated: $K_{xx}$=122.05; $k_{yy}$=119.86; $k_{xy}$=$k_{yx}$=58.08. The proper values of this tensor are: $K'_{xx}$=179.05; $K'_{yy}$=62.86. The system of principal axes is indeed oriented 44.46° in relation to the imposed direction of flow. This corresponds to the direction of the initial anisotropy.

Figure 4A:
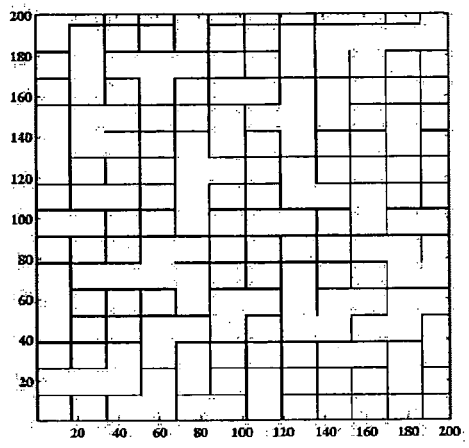
Figure 4B:
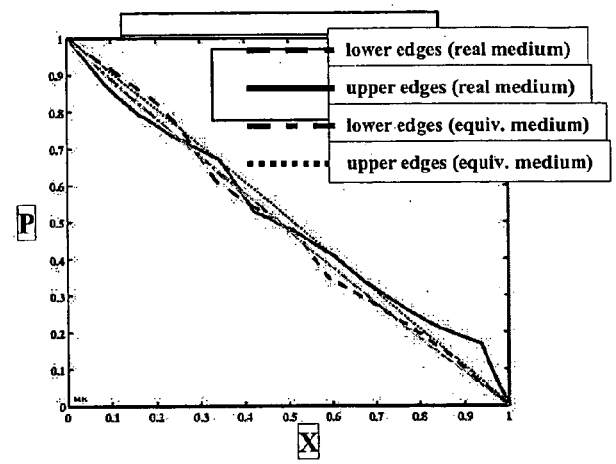
Figure 4C:
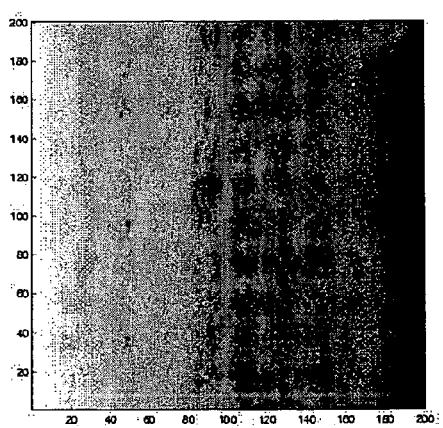
Figure 4D:
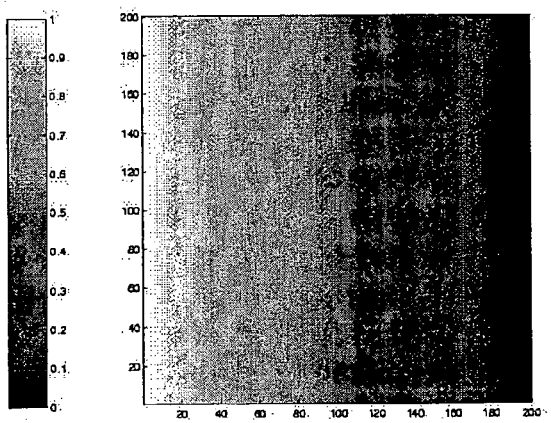

FIG. 4A shows a network of fractures of a fracture volume fraction of 10%, the permeability of the matrix being of the order of 1 Darcy whereas the permeability of the fractures is of the order of 100 Darcy (left). FIG. 4B shows the evolution of the pressure on the upper and lower edges (impermeable edges for a horizontal confined flow) for the real medium and its anisotropic homogeneous equivalent determined by means of the permeameter method. FIGS. 4C and 4D respectively show the mappings of the pressure field for the real medium and its equivalent. The components of the permeability tensor of the equivalent medium are: $K_{xx}$=5.79 D; $k_{yy}$=4.37 D; $k_{xy}$=$k_{yx}$=0.26 D. The proper values of this tensor are: $K'_{xx}$=5.83 D; $K'_{yy}$=4.32 D. The system of principal axes is rotated 9.830 in relation to the system of axis made up of the horizontal and the vertical direction.

The invention claimed is:

1. A method of determining, from known permeability measurements, all components of an absolute permeability tensor of a sample of an anisotropic porous medium, comprising the steps of:

measuring or calculating, from at least two liquid flows along at least two orthogonal directions under an imposed pressure gradient, liquid flow rates and components of transverse forces generated in the sample by passage of the liquid, the flow rates and components being brought back to unitary pressure gradients; and using a simulator to determine step by step, from an a priori numerical solution of a confined flow in a homogeneous medium, components of an equivalent tensor by means of an inverse method so that the liquid flow rates and the components of transverse forces simulated by the simulator are adjusted to measured or calculated flow rates and the components of the transverse forces.

2. A method as claimed in claim 1, wherein the liquid flow rates and the components of the transverse forces are measured by a permeameter equipped with means for measuring the transverse forces applied to the sample in response to the at least liquid flows imposed through the sample.

3. A method as claimed in claim 2, wherein the transverse forces applied to the sample in response to the liquid flows imposed through the sample are determined by measuring apparent weight variations of the sample in the permeameter when a direction of circulation of the liquid flows through the sample is alternated.

4. A method in accordance with claim 3, wherein three liquid flows are measured or calculated along three orthogonal directions.

5. A method in accordance with claim 2, wherein three liquid flows are measured or calculated along three orthogonal directions.

6. A method as claimed in claim 1, wherein the liquid flow rates and the components of the transverse forces are determined by simulation of flows in a medium, from known or estimated permeability data.

7. A method in accordance with claim 6, wherein three liquid flows are measured or calculated along three orthogonal directions.

8. A method in accordance with claim 1, wherein three liquid flows are measured or calculated along three orthogonal directions.

* * * * *